United States Patent
Abdel-Rahman

(10) Patent No.: US 6,531,877 B1
(45) Date of Patent: Mar. 11, 2003

(54) MINIATURIZED GLOW DISCHARGE ELECTRON CAPTURE DETECTOR

(75) Inventor: Mahmoud Abdel-Rahman, Newark, DE (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/961,715

(22) Filed: Sep. 24, 2001

Related U.S. Application Data

(63) Continuation-in-part of application No. 09/931,927, filed on Aug. 20, 2001, now Pat. No. 6,448,777.
(51) Int. Cl.[7] .............................................. G01N 27/62
(52) U.S. Cl. ....................................... 324/464; 324/459
(58) Field of Search ................................ 324/464, 468, 324/465, 466, 460, 459; 250/288, 382

(56) References Cited

U.S. PATENT DOCUMENTS 4,780,284 A * 10/1988 Lovelock .................... 250/283

* cited by examiner

Primary Examiner—N. Le
Assistant Examiner—James C Kerveros

(57) ABSTRACT

An ionization detector includes a unique combination of elements including a non-radioactive glow discharge source, a gas flow area designed to promote mixing of sample gas with a reagent gas, a GC column interface which directs air leaks away from the sample area, and a signal electrode designed to discriminate against ion collection. This embodiment includes a body defining a detector cavity and a sample flow area. A plurality of electrodes are disposed within the body including a glow discharge source having a first and second discharge electrode located near one end of the body, a guard electrode located longitudinally intermediate to the discharge electrode and the sample flow area, and a signal electrode disposed within a signal electrode cavity located near an end opposite to the guard electrode. A column interface depends from the body, in communication with the sample flow area. The column interface includes a reagent inlet and a purge outlet which extend laterally from a longitudinal portion of the column interface. A column from a GC extends through the longitudinal portion and is partially disposed within the sample flow area.

22 Claims, 4 Drawing Sheets

MINIATURIZED GLOW DISCHARGE ELECTRON CAPTURE DETECTOR

CROSS-REFERENCE TO RELATED APPLICATION(S)

This application is a Continuation-in-Part of U.S. application Ser. No. 09/931,927 and now U.S. Pat. No. 6,448,777 filed on Aug. 20, 2001, the contents of which are hereby incorporate herein in its entirety.

FIELD OF THE INVENTION

The present invention relates to ionization detector devices. More specifically, the present invention relates to an apparatus and a method of making a glow discharge electron capture detector having a small detection volume.

BACKGROUND OF THE INVENTION

Ionization detectors are well known in the art. These detectors are typically used in conjunction with a gas chromatography system ("GC") in order to detect the presence of specific compounds. Sample gas flowing from the GC is typically received by an ionization detector where it undergoes an ionization process. In this process, molecular compounds within the sample gas are ionized and the ionization of these compounds is detected and measured by an electrode within the ionization detector.

One such ionization detector is called an Electron capture detector ("ECD"). An ECD is a type of ionization detector which offers high sensitivity and high selectivity towards electrophilic compounds and is widely used for detecting trace amounts of pesticides in biological systems and in food products. Such compounds typically contain halogens which readily combine with free electrons that are created within the ECD. The resulting decrease in free electrons in the ECD is used by the ECD as an indication of the concentration of the compounds in a sample.

In more traditional methods, the creation of free electrons within the ECD is typically achieved through the use of a radioactive source, such as radioactive Nickel 63. A detector gas capable of producing thermal electrons such as nitrogen flows through a chamber containing the radioactive source. The radioactive radiation causes ionizing particles, in the form of positive ions and free low energy electrons, to be produced. These free electrons are readily accepted by electrophilic molecules within the sample gas, otherwise referred to as analytes.

The chamber also typically includes an electrode which detects a current flowing within the ECD produced by the flow of free electrons. The level of this current provides an indication of the concentration of analytes within the sample gas.

While prior ECD work for their intended purpose, these devices have a number of drawbacks that need improvement and modification. One such drawback is the use of radioactive source for ionization. The use of a radioactive source requires specialized procedures for handling and use. These additional procedures add significant cost and time to operate the GC. Furthermore, the use of a radioactive source within the ECD poses a potential health risk to the operators of the GC.

There are other types of ionization detectors which do not use the radioactive materials employed by typical ECD. However, these non-radioactive ionization detectors typically do not have a large linear dynamic range of like that typically found with state of the art ECD.

Current ECDs, as well as most ionization detectors, also typically require relatively large detector volumes of approximately 150 $\mu$L or greater. As a result of the relatively large detector volumes required, large amounts of sample gas and high gas flow rates are also required to properly operate the ECD. This requirement can be problematic for a GC, especially for ultrafast and portable gas chromatographs.

Furthermore most ionization detector designs are also plagued by structural breakdowns which affect the ECD's accuracy. Ambient air leaks often develop within the detector seals. Ions often collect on the signal electrode surface, as a result of its direct exposure to sample gas flows. These type of structural breakdowns can significantly affect the accuracy and reliability of an ECD.

Therefore a need exists for an apparatus and method which overcomes the aforementioned problems currently known in the art.

BRIEF SUMMARY OF THE INVENTION

The present invention provides an advantage in ionization detector design by providing an ECD that does not utilize radioactive material as a source for ionization particles. Such an ECD reduces the time and expense attributed towards the handling requirements of the radioactive material. Furthermore, the use of non-radioactive materials eliminates a potential health risk for the operator of the GC.

The present invention also provides an ECD having a smaller detector volume relative to those ECDs known in the art. This enables the present ECD to achieve greater accuracy without requiring the presence of larger amounts of analytes and high gas flow rates.

The present invention also provides an ionization detector which minimizes the effect of ambient air leaks on the detector's accuracy.

Accordingly, the present invention avoids the drawbacks of prior ionization detectors and provides additional benefits as a result of its design. This improvement over the prior art is achieved through the use of a unique combination of elements in its design.

In one embodiment, the ionization detector includes a unique combination of elements including a non-radioactive glow discharge source, a gas flow area designed to promote mixing of sample gas with a reagent gas, a GC column interface which directs air leaks away from the sample area, and a signal electrode designed to discriminate against positive ion collection.

One embodiment includes a body defining a detector cavity and a sample flow area. The detector cavity is essentially funnel-shaped and extends longitudinally through the body. The sample flow area includes a frusto-conical passage in communication with the detector cavity.

One embodiment also includes a plurality of electrodes disposed within the body. The electrodes include a glow discharge source comprising a first and second discharge electrode located near one end of the body, a guard electrode located longitudinally intermediate to the discharge electrode and the sample flow area, and a signal electrode disposed within a signal electrode cavity located near an end opposite to the discharge electrode.

A column interface depends from the body and is in communication with the sample flow area. The column interface includes a reagent inlet and a purge outlet which extend laterally from a longitudinal portion of the column interface. A column from a GC extends through the longitudinal portion and is partially disposed within the sample flow area.

While multiple embodiments are disclosed, still other embodiments of the present invention will become apparent to those skilled in the art from the following detailed description, wherein is shown and described only the embodiments of the invention, by way of illustration, of the best modes contemplated for carrying out the invention. As will be realized, the invention is capable of modifications in various obvious aspects, all without departing from the scope of the present invention. Accordingly, the drawings and detailed description are to be regarded as illustrative in nature and not restrictive.

DETAILED DESCRIPTION OF THE INVENTION

The present invention is an ionization detector that includes a unique combination of elements including a non-radioactive glow discharge source, a gas flow area designed to promote mixing of sample gas with a reagent gas, a GC column interface which directs air leaks away from the sample flow area, and a signal electrode designed to discriminate against positive ion collection.

Figure 1:
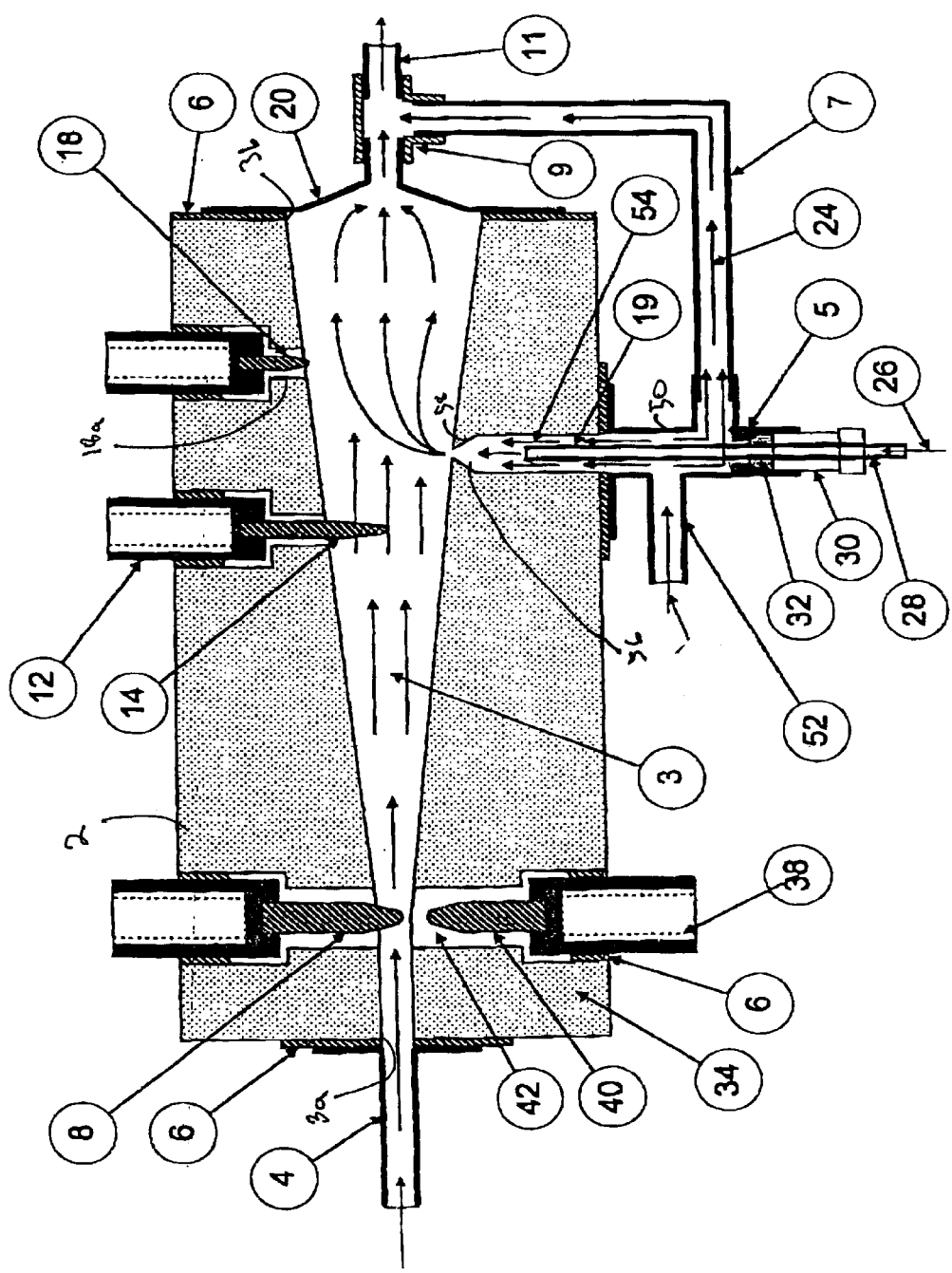
FIG. 1 is a schematic diagram of one embodiment of the present invention.

FIG. 1 shows a schematic diagram of one embodiment of the present invention. This embodiment includes a body 2 defining a detector cavity 3 and a sample flow area 54. The detector cavity 3 is essentially funnel-shaped and extends longitudinally through the body 2. The detector cavity 3 defines a first body opening 3a and a second body opening 3b located at opposite ends of the body 2, with the first body opening 3a having a diameter that is less than the second body opening 3b.

In an embodiment, the sample flow area 54 is located along an end of the body 2 near the second body opening 3b. The sample flow area 54 includes a turbulence area 56 which promotes the mixing of gases flowing therethrough. In this embodiment, the turbulence area 56 includes a frusto-conical passage 58 in communication with the detector cavity 3.

In an embodiment, a glow discharge source is positioned within the cavity to promote ionization. The glow discharge source includes a first 8 and second 40 discharge electrode. In this embodiment, the discharge source (not shown) is a DC power supply and the first and second discharge electrodes are respectively a cathode 8 and an anode 40. The cathode and anode can be made of platinum or a refractory metal, such as molybdenum, to resist corrosion and sputtering. Other discharge sources may be used that do not require the use of a cathode 8 and an anode 40.

Figure 4:
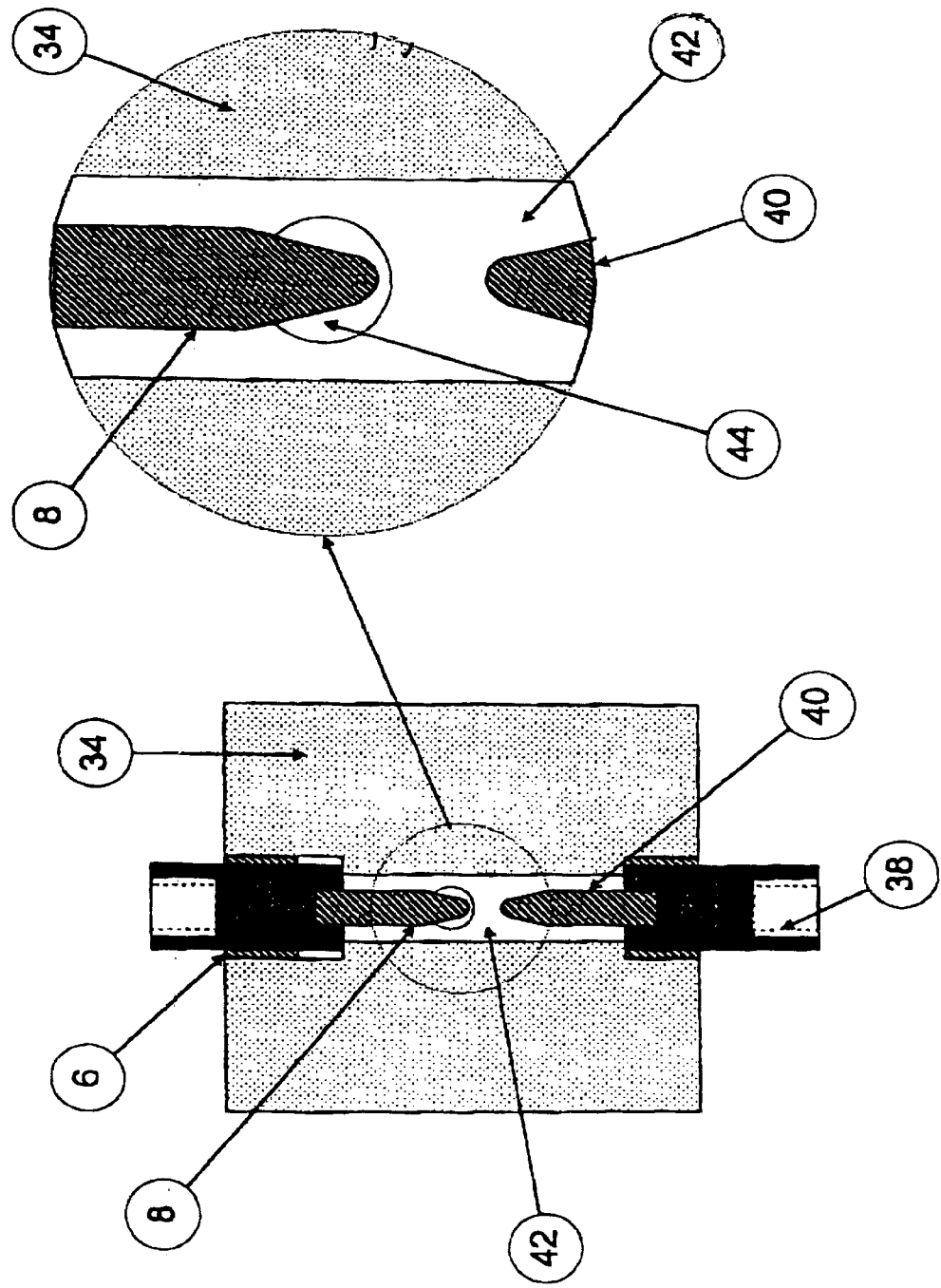
FIG. 4 is an enlarged cross-sectional view of a glow discharge source of FIG. 2.

FIG. 4 is a cross-sectional view of the detector 1 taken at the center of the discharge electrodes 8 and 40 and perpendicular to the view of FIG. 1. A bore 42 larger than the diameter of the discharge electrodes 8 and 40 allows for sufficient spacing between the gas discharge and the ceramic walls without enlarging the detector cavity cross-sectional area 44. This cross section area 44 is kept small to increase gas linear velocity and inhibit sample back diffusion. The cathode 8 is positioned so that it extends laterally across the detector cavity to produce increased ionization.

Figure 3:
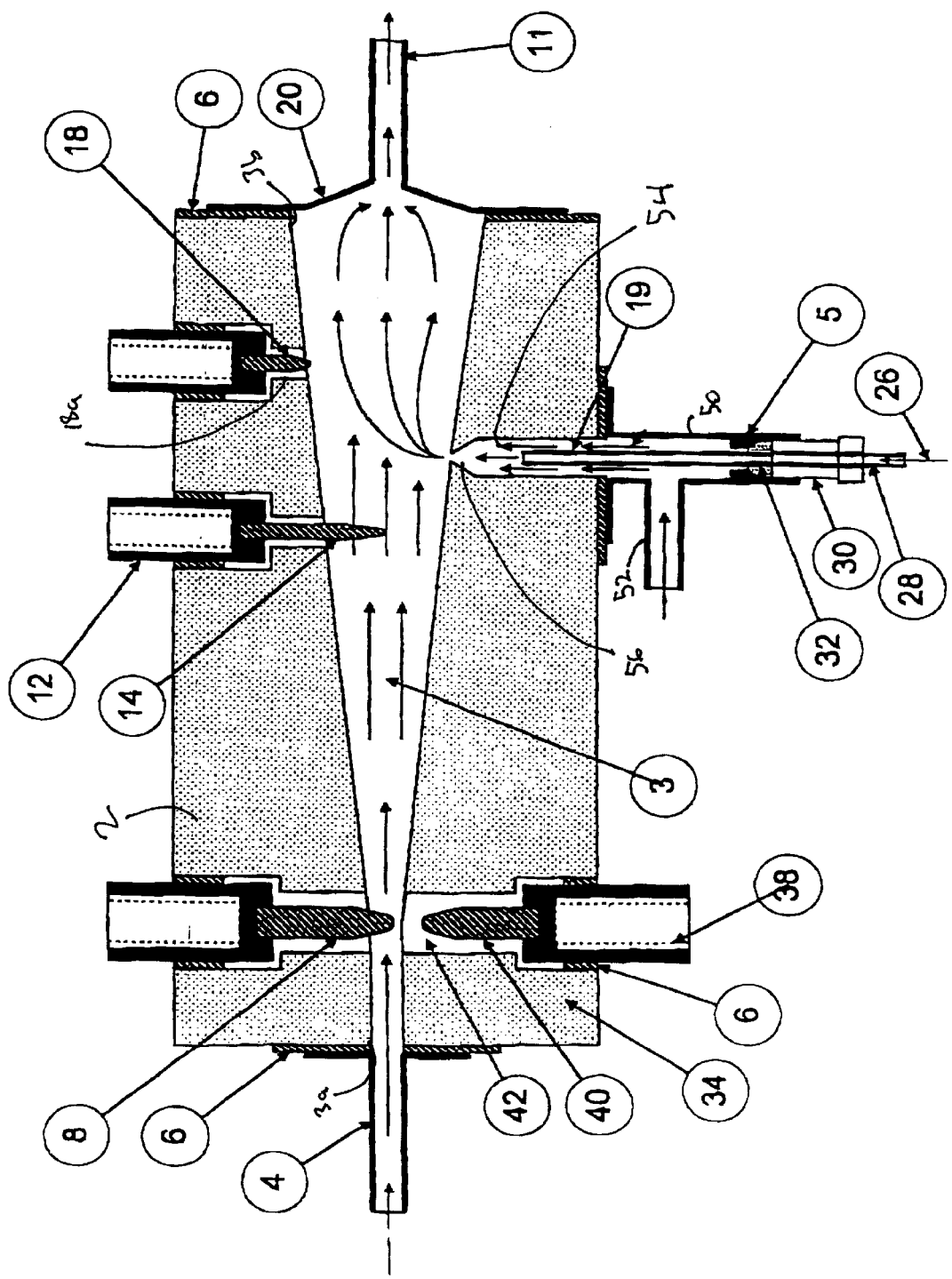
FIG. 3 schematic diagram of an alternate embodiment of the present invention.

As shown in FIGS. 1 and 3, in an embodiment, a guard electrode 14 extends at least partially within the detection cavity 3. The guard electrode 14 is located longitudinally intermediate to the discharge electrodes and the sample flow area 54. The guard electrode can also be made of platinum or a refractory metal, such as molybdenum, to resist corrosion and sputtering.

A signal electrode 18 is disposed within a signal electrode cavity 18a, with both positioned longitudinally intermediate to the sample flow area 54 and the second opening 36. The signal electrode cavity 18a is in communication with the detector cavity 3 and functions to shield the signal electrode 18 from gas flow within the detector cavity 3. By shielding the signal electrode 18, the number of positive ions which collect on its surface is significantly reduced.

As shown in FIG. 1, in an embodiment, a column interface 50 depends from the body, in communication with the sample flow area. The column interface includes a reagent inlet 52 and a purge outlet 7 which extend laterally from a longitudinal portion 50a of the column interface 50. A column 28 from a GC extends through the longitudinal portion 50a and ends partially disposed within the sample flow area 54. As shown in FIG. 3, the column interface can also be embodied without a purge outlet.

Operation

In operation, a discharge gas (otherwise referred to as detector gas) enters the detector 1 through an inlet interface 4. The discharge gas can be any noble gas. In this embodiment, the discharge gas 2 is helium. The discharge gas 2 sweeps through the detector cavity 3 passing by the discharge electrodes 8 and 40. The discharge gas completes its travel through the detector cavity 3 and exits through a vent interface 20 where it combines in a vent tee 9 and exits through vent tube 11. A gas sample to be tested enters the sample flow area through the chromatographic column 28. A reagent gas (otherwise referred to as a dopant) flow through the reagent inlet and the column interface 50 to enter the sample flow area 54.

Figure 2:
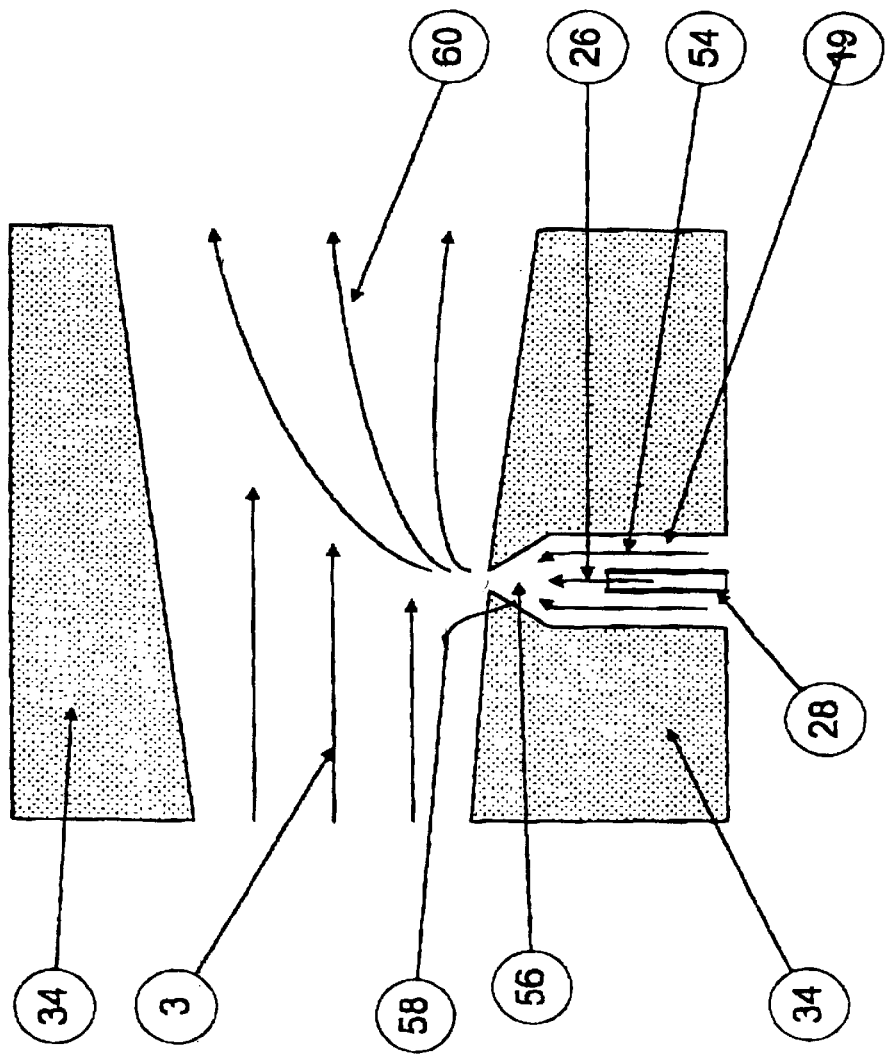
FIG. 2 is an enlarged cross-sectional view of a sample flow area of FIG. 1.

As shown in FIG. 2, as the two gases flow into the sample flow area 54 the frusto-conical passageway 58 leading into the detector cavity 3 forces the two gases to converge into each other. This creates a mixing action that thoroughly combines the reagent and the sample gas prior to entering the detector cavity 3. This mixing action leads to consistent operation and repeatable results.

In order to prevent sample analytes from diffusing back towards the discharge electrodes, the detector cavity 3 is funnel shaped, as shown in FIGS. 1 and 3.

As shown in FIG. 1, part of the reagent gas is used as a purge gas which flows through purge outlet 7 and exits through vent tube 11. This purge gas keeps small air leaks developing at the column nut 30 and column ferrule 32 from disturbing the detector operation by forcing air emanating from these locations away from the detector cavity 3 and into the purge outlet 7. It also diverts volatile gasses emanating from the polymeric column ferrule 32 into the purge outlet 7.

As shown in FIG. 4 an area of discharge 46 where ionizing particles, such as UV photons and metastable atoms are created at the tip of the discharge electrode 8. Maximizing the projection of that area into the detector cavity 3 helps to maximize sample analyte ionization and thus increase detector sensitivity.

An electrical discharge excites the detector gas to glow and give off high energy photons, and excite part of detector gas atoms to a metastable level. If the energy of an incoming photon is high enough, photo-excitation can occur to such an extent that an electron is completely removed from its molecular orbital. This is called photo-ionization. A typical photo-ionization reaction resembles the following:

$$R + h\nu \rightarrow R^+ + e^-$$

Also, the metastable atoms can transfer their energy to other molecules during tertiary collisions. If the ionization potential of an analyte molecules is lower than the energy of the photon or the metastable atom, the bombarded or colliding molecule is ionized.

The reagent gas, usually methane, is ionized by the helium discharge, producing thermal electrons. The flow of thermal electrons within the cavity created between guard electrode 14 and bond interface 20 is detected by the signal electrode 18. Electron-capturing analyte present in the detector cavity capture these thermal electrons thereby reducing the detected current. Analyte concentration can then be determined based on the level of current present within the detector cavity. This correlation between the level of current and analyte concentration can be achieved in a number of ways, including but not limited to, the following examples.

In a DC mode, signal electrode 18 assumes a positive DC voltage. The detector 1 response to the presence of analyte is directly measured by the current collected by the signal electrode.

In a constant frequency mode, signal electrode 18 is positively pulsed at a constant frequency. The detector 1 response is measured by the average current collected by the signal electrode 18.

The preferred mode of operation is a constant current mode because it is able to achieve the widest dynamic range. In a constant current mode, signal electrode 18 is positively pulsed at a rate sufficient to collect a preset constant average current. This is accomplished via a feedback loop that increases or decreases the pulse rate based on the deviation from the preset constant average current. In the presence of analyte, less electrons are present and the pulsing rate has to be increased to keep the average current constant. The detector response is measured by measuring the pulsing rate.

In all modes guard electrode 14 and bond interface 20 are electrically grounded to establish the appropriate electric field enabling signal electrode 18 to collect free electrons generated within the detector cavity 3.

Manufacture

To make an embodiment of the present invention, such as that shown in FIG. 1, a body material, such as ceramic is provided. Because ceramic can withstand severe mechanical and thermal loads, and it also resists abrasion and chemical attack, it is a preferable material for the body 3. In one embodiment, the ceramic material is of high electrical resistivity in order to minimize the electrical leakage current between the signal electrode and the other electrodes and metallic connectors.

Different ceramic materials that may be utilized by the present invention, include, but are not limited to alumina, silicon nitride, silicon carbide, zirconia and magnesia. Alumina is a widely used advanced ceramic material. It has very good performance in terms of wear resistance, corrosion resistance and strength at a reasonable price. In one embodiment, the alumina used is of a high purity with a low glass content. Silicon nitride has good thermal shock resistance properties. It also has low density, high strength, low thermal expansion and good corrosion resistance and fracture toughness. Silicon carbide has high corrosion resistance. It also retains its strength at temperatures as high as 1400° C. and has good wear resistance and thermal shock resistance properties. Zirconia has high strength and toughness at room temperature. The fine grain size allows for extremely smooth surfaces and sharp edges. Magnesia shares these properties and has very high electrical resistivity.

In one embodiment, the body material is then machined with high precision tools to form the body 34 of the detector 1. The body 34 of the detector 1 is machined to have a detector cavity 3, a column bore 19 and a plurality of bores in which the electrodes 8, 40, 14 and 18 fit. Using ceramics with high precision tooling, the volume of the detector cavity 3 can be created to have a volume as small as approximately 5 to 10 μL. Larger volumes from 10 μL or greater can also be easily achieved. The body surface can then be prepared for bonding to the other components.

In one embodiment, the areas 6 of the body 3 that are to be bonded to the other components are metalized using moly-manganese or tungsten-manganese systems. The electrodes 8, 40, 14 and 18 can be bonded to the cup-shaped holders 12 using a method of bonding, such as vacuum brazing. The cup-shaped holders 12, the inlet interface 4, the column interface 50 and the vent interface 20 may then be bonded to the body 34 at the areas that have been metalized.

In one embodiment, the body 2 of the detector 1 is metalized in areas 6 needed for vacuum brazing. Inlet interface 4, column interface 5 and vent interface 20 are made of a metal that is easy to braze to the body 34, such as Kovar®. In one embodiment, a metallizing strip (not shown) is deposited on the surface of the ceramic body 34 to connect second discharge electrode 40 to guard 14 electrically through their respective holders 12 in order to simplify final detector assembly.

In one embodiment, each electrode 8, 40, 14 and 18 is vacuum brazed to a cup-shaped holder 12. The holders 12 are made with threads 38 to allow for easy extension to the electrical connections, and are made of a metal that is easy to braze to ceramic. In one embodiment, the cup-shaped holders 12 can be made of Kovar® alloy.

Kovar® alloy is a vacuum melted, Fe—Ni—Co, low expansion alloy whose chemical composition is controlled within narrow limits to assure precise uniform thermal expansion properties. Kovar® alloy is well known by those skilled in the art for making hermetic seals with ceramic materials. Kovar® is typically used in applications such as power tubes, transistors, diodes, and integrated circuits.

The proper electrical connections may then be made with the threaded portions 38 of the cup-shaped holders 12. A purge outlet 7, which acts as a pathway for the purge gas, can be bonded to the column interface 50 and a vent tee 9. The vent tee 9 can be bonded to the vent interface 20, the purge outlet 7 and the vent tube 11. The bonding of the electrodes and interfaces to the body 34, in conjunction with the purge gas pathway, create a hermetically sealed discharge electron capture detector.

Metallizing of ceramics is a highly technical process. In one embodiment, metallizing involves mixing finely milled powders of molybdenum and molybdenum oxide or tungsten and tungsten oxide with manganese and manganese oxide in a solvent slurry. The slurry can then be brushed or screened onto a clean surface, such as a ceramic body 34, air dried then fired into the surface in a wet hydrogen atmosphere between 1250 and 1700 degrees C. The resulting adherent metalized coating can then be electroless plated or electroplated with nickel and then be available to bond to matching metal parts through vacuum or protective atmosphere brazing using standard brazing alloys. This combination of metalizing and brazing is known in the trade as sintered metal powder seals.

Vacuum brazing is a process well known in the art that creates a bond that is leak tight, non-corrosive, and stronger than alternative joining methods. The first step is positioning together the parts to be joined. Because of tight tolerances, many components fit tightly together and are ready for brazing filler material to be applied to the joining area. The second step is applying the braze alloy to the joining area. Most braze joint areas lend themselves to a slurry of braze alloy powder and a gel binder. The slurry is often applied using needle point tips with foot controlled pneumatic pumps supplying the alloy. Other alloy forms, such as wire, preforms, or foil can be manually applied to the braze area. The final step, vacuum furnace treatment, can be a programmed computerized cycle based on the component material, size or quantity of assemblies, and alloy composition. The vacuum thermal process can include a heat up, preheat, holding period, braze alloy solidification, and quenching steps. Vacuum brazing simultaneously combines bonding, cleaning, and heat treating in one process.

Normally, the brazing of ceramics to metals or to themselves is a difficult matter since standard brazing alloys will not wet ceramics directly. Three options that exist for joining ceramics to metal or to themselves are the aforementioned sintered metal powder seals, active metal brazing, and fused oxide seals.

Active metal brazing involves filler metals containing various percentages of titanium and/or zirconium with other alloying elements. The active metals chemically combine with the oxygen in alumina ceramics or with the carbon or nitrogen in carbides or nitrides to form a bond with themselves or with common metals such as stainless steel, copper, steel, or Kovar. The atmosphere used for active metal brazing is normally a vacuum or inert gas such as helium or argon.

Fused oxide seals are created between two oxide containing ceramic surfaces, such as aluminas, or between oxide ceramics and metals. A suspension of finely ground metallic oxides such as $MnO_2$, $SiO_2$, and $Al_2O_3$ is applied to the seal interface, or preformed washers of this composition are placed between the parts to be sealed, and the assembly is heated in an inert gas atmosphere for a period of approximately 1 to 15 minutes at temperatures ranging from approximately 1200 degrees C. to 1500 degrees C. The joined assemblies can then be cooled at a rate rapid enough to prevent complete crystallization or devitrification of the joint. The mix of seal oxides can be modified to match the expansion coefficients of the ceramics or ceramics and metals.

The advantage of the fused oxide seal is that only one firing operation is needed to complete the seal and the seal is rugged both mechanically and thermally.

Although the present invention has been described with reference to preferred embodiments, persons skilled in the art will recognize that changes may be made in form and detail without departing from the spirit and scope of the invention.

In the claims:

1. An ionization detector comprising:
   a body defining a detector cavity and a sample flow area separate from the detector cavity, the sample flow area shaped to promote mixing of gases flowing therein prior to entrance of the gases into the detector cavity; and
   a glow discharge source at least partially disposed within the cavity.

2. The detector of claim 1, wherein the detector cavity is funnel shaped and defines a first opening and a second opening.

3. The detector of claim 2, wherein the glow discharge source is adjacent to the first openings and the sample flow area is adjacent to the second opening.

4. The detector of claim 1, wherein the body defines a signal electrode cavity in communication with the detector cavity, and further comprising a signal electrode disposed within the signal electrode cavity.

5. The detector of claim 1, and further comprising a column interface with a column disposed axially within the column interface and extending to the sample flow area, a reagent inlet, and a purge outlet which directs gas away from the sample flow area.

6. The detector of claim 5, wherein the flow area includes a frusto-conical shaped passage extending to the cavity, the passage promoting mixing of gases flowing therethrough.

7. The detector of claim 1, and further comprising a guard electrode disposed at least partially within the detector cavity, and longitudinally positioned intermediate of the discharge electrode and the sample flow area.

8. The detector of claim 1, wherein the body is ceramic and of a single piece construction.

9. The detector of claim 1, wherein the detector cavity has a volume of 10 to 5 micro-liters.

10. The detector of claim 1, wherein the glow discharge source includes a pair of discharge electrodes.

11. An ionization detector comprising:
    a body defining a detector cavity, a sample flow area shaped to promote mixing of gases flowing therein, and a signal electrode cavity;
    a column interface in communication with the sample flow area, the column interface including a column disposed axially within the column interface and extending to the sample flow area, a reagent inlet, and a purge outlet which directs gas away from the sample flow area;
    a glow discharge source at least partially disposed within the cavity; and
    a signal electrode disposed within the signal electrode cavity.

12. The detector of claim 11, wherein the detector cavity is funnel-shaped and extends longitudinally across the body defining a first opening and a second opening, the diameter of the first opening being less than the diameter of the second.

13. The detector of claim 11 and further comprising a discharge gas inlet connected adjacent to the first opening and a vent interface connected adjacent to the second opening.

14. The detector of claim 12, wherein the discharge glow source includes a discharge electrode disposed within the detector cavity adjacent to the first opening.

15. The detector of claim 13, and further comprising a guard electrode disposed at least partially within the detector cavity, and longitudinally positioned intermediate to the discharge electrode and the sample flow area.

16. The detector of claim 14, wherein the purge outlet is in communication with the vent interface.

17. A method of manufacturing an ionization detector comprising:
   forming a body having a detector cavity, a sample flow area shaped to promote mixing of gases flowing therethrough, and a signal electrode cavity;
   disposing a glow discharge source within the detector cavity;
   attaching a column interface in communication with the sample flow area; and
   disposing a signal electrode within the signal electrode cavity.

18. The method of claim 17, wherein the body is formed of a ceramic material.

19. The method of claim 17, wherein the step of disposing a glow discharge source includes the step of disposing a glow discharge electrode within the cavity.

20. The method of claim 17, and further comprising the additional step of disposing a guard electrode at least partially within the cavity longitudinally intermediate to the glow discharge electrode and the sample flow area.

21. The method of claim 17, wherein the body is formed so that the cavity is funnel-shaped and has a volume of 10 micro-liters or less.

22. An ionization detector comprising:
   a body defining a detector cavity and a sample flow area separate from the detector cavity, the sample flow area shaped to promote mixing of gases flowing therein prior to entrance of the gases into the detector cavity;
   a glow discharge source at least partially disposed within the cavity; and
   a column interface connected to the sample flow area.

* * * * *